United States Patent
Errico et al.

(10) Patent No.: US 11,331,131 B2
(45) Date of Patent: May 17, 2022

(54) FIXATION DEVICE AND METHOD OF USING THE SAME

(71) Applicant: K2M, Inc., Leesburg, VA (US)

(72) Inventors: Thomas J. Errico, New York, NY (US); Peter Newton, La Jolla, CA (US); Harry Shufflebarger, Jupiter, FL (US); Brittany Harwell, Warrenton, VA (US)

(73) Assignee: K2M, Inc., Leesburg, VA (US)

( * ) Notice: Subject to any disclaimer, the term of this patent is extended or adjusted under 35 U.S.C. 154(b) by 253 days.

(21) Appl. No.: 16/499,366

(22) PCT Filed: Mar. 30, 2018

(86) PCT No.: PCT/US2018/025387
§ 371 (c)(1),
(2) Date: Sep. 30, 2019

(87) PCT Pub. No.: WO2018/183837
PCT Pub. Date: Oct. 4, 2018

(65) Prior Publication Data
US 2021/0077167 A1 Mar. 18, 2021

Related U.S. Application Data

(60) Provisional application No. 62/478,709, filed on Mar. 30, 2017.

(51) Int. Cl.
*A61B 17/86* (2006.01)
*A61B 17/70* (2006.01)
*A61B 17/88* (2006.01)
*A61B 17/00* (2006.01)
*A61B 17/56* (2006.01)

(52) U.S. Cl.
CPC .......... *A61B 17/863* (2013.01); *A61B 17/862* (2013.01); *A61B 17/8635* (2013.01); *A61B 17/7037* (2013.01); *A61B 17/8891* (2013.01); *A61B 2017/00862* (2013.01); *A61B 2017/564* (2013.01)

(58) Field of Classification Search
CPC .............. A61B 17/8625; A61B 17/863; A61B 17/8635
See application file for complete search history.

(56) References Cited

U.S. PATENT DOCUMENTS

| | | |
|---|---|---|
| 5,334,204 A | 8/1994 | Clewett et al. |
| 9,482,260 B1 * | 11/2016 | Krause ............... A61B 17/8625 |
| 2011/0144703 A1 | 6/2011 | Krause et al. |

(Continued)

OTHER PUBLICATIONS

International Search Report for PCT/US2018/025387, dated May 14, 2018, 2 pages.

*Primary Examiner* — Olivia C Chang
(74) *Attorney, Agent, or Firm* — Lerner, David, Littenberg, Krumholz & Mentlik, LLP (57) ABSTRACT

A fixation device includes a head, a tapered body coupled to the head and extending along a central longitudinal axis, and a flexible tail extending distally from the tapered body and defining a central bore therethrough. The flexible tail is movable from an initial configuration aligned with the central longitudinal axis to a deflected configuration that extends away from the central longitudinal axis when a force is applied to the flexible tail.

18 Claims, 4 Drawing Sheets

(56) References Cited

U.S. PATENT DOCUMENTS

2014/0163624 A1     6/2014  Siegal et al.
2017/0095279 A1*    4/2017  Bare .................... A61B 17/863
2018/0092677 A1*    4/2018  Peterson .............. A61B 17/863

* cited by examiner

FIG. 5

FIXATION DEVICE AND METHOD OF USING THE SAME

CROSS-REFERENCE TO RELATED APPLICATION

This application is a national phase entry under 35 U.S.C. § 371 of International Application No. PCT/US2018/025387, filed Mar. 30, 2018, which claims the benefit of the filing date of U.S. Provisional Patent Application No. 62/478,709, filed Mar. 30, 2017, the disclosures of which are hereby incorporated herein by reference.

TECHNICAL FIELD

The present disclosure relates generally to surgical devices, and more particularly, to fixation devices having a flexible portion and methods for securing the fixation devices to osseous tissue.

BACKGROUND

Spinal pathologies, whether the result of genetic or developmental irregularities, trauma, chronic stress, tumors, or disease can limit the spine's range of motion or threaten critical elements of the nervous system housed within the spine. A variety of systems to correct the alignment of the spinal vertebrae involving the implantation of artificial assemblies in or on the spine have been devised.

The mechanical hardware used to immobilize the spinal column typically involves a series of bone screws and metal rods or plates. When the spine surgery is performed posteriorly, it is common practice to place bone screws into the vertebral bodies and then connect a metal rod between the bone screws, thus creating a rigid structure between adjacent vertebral bodies. In some cases, these devices may be permanently implanted in the patient. In other cases, the devices may be implanted only as a temporary means of stabilizing or fixing the bones or bone fragments, with subsequent removal when no longer needed.

When using bone screws, a clinician directs the bone screw into a vertebra. The vertebra is composed of a hard, strong ossified shell surrounding soft osseous tissue. The pedicle is a narrow passage way which connects proximal and distal sides of the vertebra through the vertebral body. The pedicle is a challenging area for the clinician to traverse since the spinal cord, a very delicate tissue and nerve connector for the entire body, is located medial to the pedicle. There are also nerve roots and organs extending lateral to the pedicle. Therefore, a clinician puts care into directing the bone screw in the correct path through the vertebra. Sometimes a clinician may want to redirect the bone screw, in which case the clinician would need to remove the original bone screw, and redirect the bone screw through the pedicle. Redirection removes more bone and can compromise fixation of the bone screw or completely damage the vertebral body, rendering it unusable as a point of device fixation.

Therefore, a fixation device that can help a clinician improve efficiency and/or accuracy of inserting fixation devices, such as a bone screws, into a vertebra, while also protecting the spinal cord and minimizing the need for redirection.

SUMMARY

In accordance with an aspect of the present disclosure, a fixation device includes a head, a tapered body coupled to the head and extending along a central longitudinal axis, and a flexible tail extending distally from the tapered body and defining a central bore therethrough. The flexible tail is movable from an initial configuration aligned with the central longitudinal axis to a deflected configuration that extends away from the central longitudinal axis when a force is applied to the flexible tail.

The head portion may define an opening therein. The central bore may be disposed distal to and in fluid communication with the opening of the head and extend to a distal end of the fixation device. The head portion may have a cylindrical shape including a threaded outer surface.

A neck may interconnect the head and the tapered body.

The tapered body may include helical threads disposed on an outer surface thereof that taper distally towards the flexible tail. The tapered body may have a length extending at least a quarter of an overall length of the fixation device. The tapered body may have a length extending at least a half of an overall length of the fixation device.

The flexible tail may include a shaft portion having a cut formed therein that follows a helical path around the shaft portion. The cut may extend from a proximal end to a distal end of the shaft portion of the flexible tail. The cut may define alternating trapezoidal shapes along the shaft portion.

The flexible tail may include a tip portion extending distally from the shaft portion. The tip portion may taper distally to a distal end of the fixation device. The tip portion may include a plurality of facets defining edges therebetween.

The flexible tail may have a length extending at least a quarter of an overall length of the fixation device. The flexible tail may have a length extending at least a half of an overall length of the fixation device.

The central bore may include a proximal portion having a first diameter and a distal portion having a second diameter smaller than the first diameter. The proximal portion of the central bore may be disposed within a shaft portion of the flexible tail, and the distal portion of the central bore may be disposed within a distal tip of the flexible tail.

In accordance with an aspect of the present disclosure, a method of securing a fixation device to osseous tissue includes inserting a flexible tail and a tapered body of a fixation device into an insertion hole in osseous tissue, the flexible tail disposed in an initial configuration aligned with a central longitudinal axis extending through the tapered body and movable to a deflected configuration that extends away from the central longitudinal axis if the flexible tail encounters a force during insertion.

The method may further include applying a rotational force to a head of the fixation device to engage helical threads disposed on an outer surface of the tapered body with the osseous tissue.

Other aspects, features, and advantages will be apparent from the description, drawings, and the claims.

BRIEF DESCRIPTION OF THE DRAWINGS

The accompanying drawings, which are incorporated in and constitute a part of this specification, illustrate embodiments of the present disclosure and, together with a general description of the disclosure given above, and the detailed description of the embodiments given below, serve to explain the principles of the present disclosure, wherein.

DETAILED DESCRIPTION

Exemplary embodiments of the present disclosure are discussed herein below in terms of a fixation device for use in osseous tissue. While the principles of the present disclosure are described below with respect to the insertion of the fixation device into a pedicle of a vertebra during orthopedic spine surgery, it should be understood that the fixation device of the present disclosure is suitable for insertion into any osseous tissue, such as the iliac of the pelvis, and use in a variety of surgical procedures. Accordingly, a person of ordinary skill in the art will readily appreciate that the size and/or shape of the fixation device, or components thereof, can be modified for proper alignment and fit within a desired osseous tissue. For example, the fixation device may be shorter or longer in length than a traditional bone screw. As another example, if the osseous tissue is a pedicle of a vertebra, the fixation device can be sized and dimensioned so that it would not extend into the intervertebral space.

Embodiments of the present disclosure will now be described in detail with reference to the drawings in which like reference numerals designate identical or corresponding elements in each of the several views. Throughout this description, the term "proximal" refers to a portion of a system, a device, or component thereof, that is closer to a clinician, and the term "distal" refers to the portion of the system, the device, or component thereof, that is farther from the clinician. The term "clinician" refers to a doctor (e.g., a surgeon), a nurse, or any other care provider, and may include support personnel.

Figure 1:
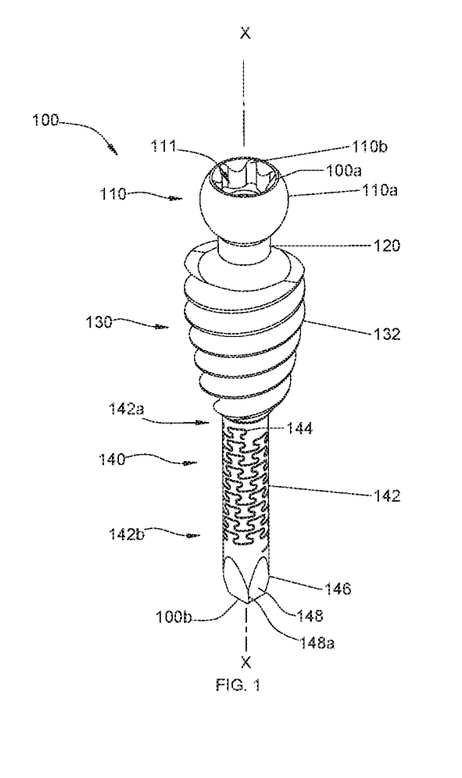
FIG. 1 is a perspective view of a fixation device in accordance with an embodiment of the present disclosure.
Figure 2:
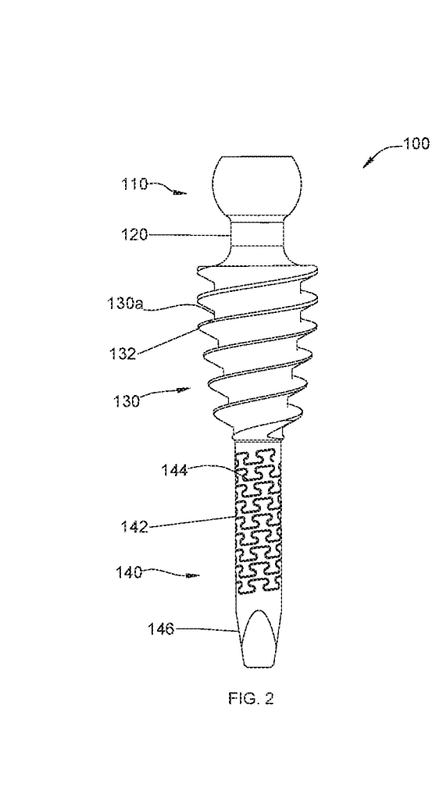
FIG. 2 is a side view of the fixation device of FIG. 1.
Figure 3:
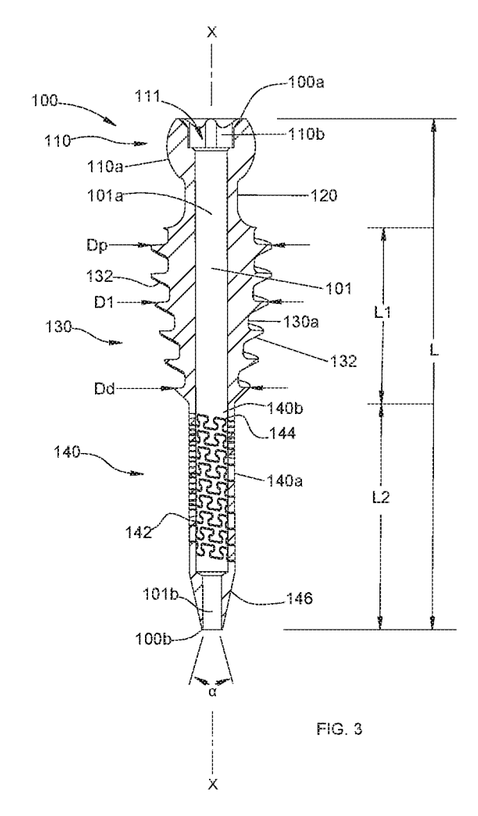
FIG. 3 is a cross-sectional view of the fixation device of FIG. 1.

Referring now to FIGS. 1-3, a fixation device or flexible screw 100 in accordance with an embodiment of the present disclosure is shown. The fixation device 100 is suitable for use during the treatment of bones (e.g., to fix the position of a bone, or portions thereof, or to maintain alignment of bone(s)), and may provide a point of fixation and/or facilitate the attachment of other devices (e.g., rods, plates, etc.) to the bone(s).

The fixation device 100 extends along a central longitudinal axis "X" and includes a head 110, a neck 120, a tapered body 130, and a flexible tail 140. The fixation device 100 may be integrally formed (e.g., by machining, molding, etc.), or one or more of the head 110, the neck 120, the tapered body 130, and/or the flexible tail 140 may be fixedly attached (e.g., by welding, fastening, press-fitting, etc.) to an adjacent component of the fixation device 100 such that the fixation device 100 has a unitary construction.

The head 110 of the fixation device 100 has a substantially spherical or ball shape. The head 110 includes an outer surface 110a that can be roughened (e.g., textured, grooved, etc.) to enhance the grip of a clinician or the attachment of another surgical device thereto, such as a modular screw assembly (see e.g., FIG. 5) which, in turn, may be coupled to other surgical devices (e.g., rods, plates, etc.). Suitable modular screw assemblies include, for example, taper lock or set screw housing systems such as those shown in U.S. Pat. Nos. 8,814,919 and 9,393,049, and/or modular head assemblies such as those shown in Int'l Appl. No. PCT/US18/14179, the entire content of each of which is incorporated by reference herein. The head 110 can be of any shape and/or size suitable for manipulating the fixation device 100 into an osseous tissue and/or facilitating attachment of other surgical devices thereto.

Figure 6A:
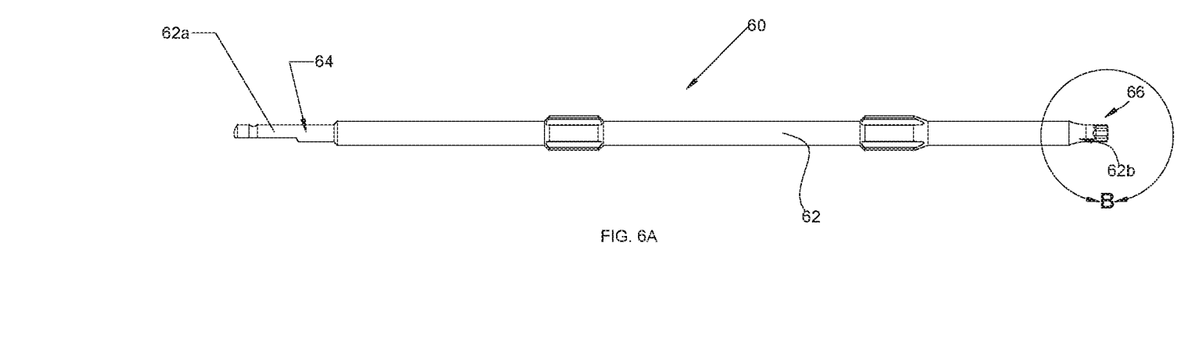
FIG. 6A is a side view of a driving instrument for rotating a fixation device of the present disclosure.

The head 110 includes an opening 111 therein that is defined by an inner surface 110b of the head 110. The opening 111 is disposed at a proximal end 100a of the fixation device 100 and is configured and dimensioned to receive a driving instrument 60 (FIG. 6A). The inner surface 110b of the head 110 may be multi-faceted (e.g., hexagonal or hexolobular in shape), keyed, or any other suitable configuration that is engageable with a suitable driving instrument to enable the driving instrument to control rotation of the fixation device 100 and/or aid in the insertion or removal of the fixation device 100 into or out of osseous tissue.

The neck 120 extends between the head 110 and the tapered body 130. The neck 120 has an outer transverse dimension (e.g., diameter) that is smaller than the outer transverse dimensions of the head 110 and the tapered body 130 to separate the head 110 which, as described above, may act as a connection portion of the fixation device 100 to other surgical devices, and the tapered body 130 which acts as an anchoring portion of the fixation device 100 in the osseous tissue. This allows for securing of the fixation device 100 into bone and subsequent attaching of a modular head assembly (see e.g., FIG. 5) to the head 110 due to the neck 120 maintaining a gap between the distal end of the head 110 and a surface of the bone, in addition to the spherical ball shape of the head 110. The neck 120 can flare at the transition regions of the neck 120 with the head 110 and the tapered body 130.

The tapered body 130 extends between the neck 120 and the flexible tail 140, and tapers distally towards the flexible tail 140. In embodiments, the tapered body 130 has a length "L1" extending at least a quarter of an overall length "L" of the fixation device 100, and in some embodiments, the tapered body 130 has a length "L1" extending at least a half of the overall length "L" of the fixation device 100. In certain embodiments, the tapered body 130 has a length "L1" that is less than a quarter of the overall length "L" of the fixation device 100. It should be understood that the tapered body 130 may have any shape, size, and/or length suitable for insertion into a targeted osseous tissue. For example, the fixation device 100 may be configured and dimensioned such that when the fixation device 100 is inserted into osseous tissue, such as a pedicle of a vertebra, the tapered body 130 fits within the pedicle.

The tapered body 130 includes helical threads 132 extending from an outer surface 130a of the tapered body 130 that are configured to cut and/or thread into osseous tissue. The helical threads 132 may extend along the entire length "L1" of the tapered body 130, a portion of the length "L1" of the tapered body 130, or include regions of helical threads 132 disposed in spaced relation relative to each other along the length "L1" of the tapered body 130. The helical threads 132 can rotate clockwise (i.e., right-handed thread) or counter-clockwise (i.e., left-handed thread) about the tapered body 130. It should be understood that the configuration, number, and/or orientation of the helical threads 132 may vary depending upon, for example, the desired cutting and/or retaining characteristics desired of the fixation device 100.

In embodiments, the helical threads 132 have a major diameter "D1" ranging from about 9 mm to about 13 mm, and in some embodiments, the major diameter "D1" of the helical threads 132 ranges from about 10 mm to about 12 mm. In embodiments, the major diameter "D1" of the helical threads 132 tapers distally along the length "L1" of the tapered body 130 at a ratio of major diameter proximal "Dp" to major diameter distal "Dd" of about 1 to about 2, and in some embodiments, at a ratio of about 1.4 to about 1.7. The angle "α" of the taper, or taper angle, may vary and in embodiments, the taper angle "α" is from about 10 degrees to about 60 degrees and, in some embodiments, the taper angle "α" is from about 18 degrees to about 56 degrees.

The flexible tail 140 extends distally from the tapered body 130 to a distal end 100b of the fixation device. In embodiments, the flexible tail 140 has a length "L2" extending at least a quarter of the overall length "L" of the fixation device 100, and in some embodiments, the flexible tail 140 has a length "L2" extending at least a half of the overall length "L" of the fixation device 100. It should be understood that the flexible tail 140 may have any shape, size, and/or length suitable for insertion into a targeted osseous tissue. For example, the fixation device 100 may be configured and dimensioned such that when the fixation device 100 is inserted into osseous tissue, such as a pedicle of a vertebra, the flexible tail 140 extends only a certain amount past the pedicle such that it does not extend into the vertebral body.

The flexible tail 140 is configured and dimensioned to bend and/or flex when subjected to an applied force. The flexible tail 140 includes a shaft portion 142 having a cut or slit 144 formed therein that spirals from a proximal end 142a of the shaft portion 142 to a distal end 142b of the shaft portion 142. The cut 144 may extend along the entire length of the shaft portion 142, a portion of the length of the shaft portion 142, or include regions of cuts 144 disposed in spaced relation relative to each other along the length of the shaft portion 142. The cut 144 may be formed by, for example, laser or fluid jet cutting through exterior and interior surfaces 140a, 140b of the flexible tail 140 along a helical path around the shaft portion 142.

The cut 144 winds around the shaft portion 142 forming alternating trapezoidal shapes along the length thereof. The cut 144, however, can have any geometric configuration along a helical path such as, for example, a straight line, a sinusoidal wave, etc. The cut 144 may be a single cut (e.g., a helical cut) or a plurality of cuts defined in the shaft portion 142 of the flexible tail 140. The configuration, number, and/or orientation of the cut(s) 144 can vary depending upon, for example, the desired flexibility of the flexible tail 140. It is envisioned that the cut 144 can follow any path or line through the shaft portion 142 and/or can be any shape suitable for bending or flexing of the flexible tail 140 when an external force is applied.

A tip portion 146 of the flexible tail 140 extends distally from the shaft portion 142. The tip portion 146 tapers towards the distal end 110b of the fixation device 100, and includes a plurality of facets 148 defining edges 148a therebetween that are configured to guide the fixation device 100 into the osseous tissue. Other configurations of the tip portion 146 are contemplated. For example, the tip portion 146 may have a conical shape terminating at a pointed or blunted end.

A central bore 101 extends through the fixation device 100 and is concentric with the central longitudinal axis "X".

As specifically shown in FIG. 3, the central bore 101 is disposed distal of and in fluid communication with the opening 111 defined in the head 110, and extends through the head 110, the neck 120, the tapered body 130, and the flexible tail 140 such that the central bore 101 is open at the distal end 100b of the fixation device 100. The central bore 101 may be configured to receive, for example, a guide wire, a guide pin, or other surgical implements therethrough (not shown).

The central bore 101 includes a proximal portion 101a having a first diameter through the head 110, the neck 120, the tapered body 130, and the shaft portion 142 of the flexible tail 140 that is smaller than a diameter of the opening 111 defined in the head 110. The central bore 101 also includes a distal portion 101b having a second diameter through the tip portion 146 of the flexible tail 140 that is smaller than the first diameter of the proximal portion 101a of the central bore 101. It should be understood that the diameter of the central bore 101 may be constant or vary along any portion of the length thereof. For example, the central bore 101 may gradually taper distally from the opening 111 defined in the head 110 to the distal end 100b of the fixation device, or may have graduated/stepped diameters narrowing towards the distal end 100b. Further, the central bore 101 may be defined only in predefined portions of the fixation device 100 such as, for example, only within the flexible tail 140 or only within the shaft portion 142 of the flexible tail 140, such that the rigid components of the fixation device 100 (i.e., the head 110, the neck 120, the tapered body 130, and/or the tip portion 146) are solid and/or have high mechanical strength.

With continued reference to FIGS. 1-3, the fixation device 100 has an initial position in which the flexible tail 140 is aligned with the head 110, the neck 120, and the tapered body 130 along the central longitudinal axis "X". The fixation device 100 is movable from the initial position to a variety of deflected positions in which the flexible tail 140 is displaced relative to the central longitudinal axis "X" when and if a force is applied to the flexible tail 140. The flexible tail 140 may be configured to move linearly or non-linearly away from the central longitudinal axis "X" when an external force is applied.

In a method of using the fixation device 100 in accordance with an embodiment of the present disclosure, an insertion hole is formed in osseous tissue to perforate the ossified shell or cortical bone. A clinician drills or otherwise forms the insertion hole into the osseous tissue using known devices and techniques (e.g., punching, cutting, coring, etc.). For example, an insertion hole may be formed by preparing the surface of the osseous tissue with a burr or other like instrument and then using an awl or other like instrument to start the insertion hole in such anatomy as a pedicle of a vertebra. The insertion hole may be at the top of an isthmus of a pedicle.

The fixation device 100, disposed in the initial position of FIGS. 1-3, is then inserted into the insertion hole and driven therethrough to make a path through the soft osseous tissue or cancellous bone of the osseous tissue. A tip 66 (FIG. 6B) of a driving instrument 60 may be inserted into the opening 111 defined in the head 110 of the fixation device 100 to engage the inner surface 110b of the opening 111 to aid in the insertion of the fixation device 100 into the insertion hole and through the osseous tissue. The clinician inserts the fixation device 100 into the insertion hole until the tapered body 130 is disposed within the osseous tissue (e.g., a pedicle of a vertebra). During insertion, the flexible tail 140 navigates through the cancellous bone and will redirect itself if it encounters a force, such as hitting cortical bone. For example, the flexible tail 140 may bend as it approaches the cortical bone to remain within the cancellous bone of the osseous tissue.

The fixation device 100 may be manipulated by imparting a rotational force thereto. A rotational force may be applied to the head 110 by placing the tip 66 (FIG. 6B) of the driving instrument 60 into the opening 111 of the head 110, as described above, and applying a rotational force to the driving instrument 60 that rotates the fixation device 100 about the central longitudinal axis "X" so that the helical threads 132 of the tapered body 130 engage with the osseous tissue (e.g., the pedicle). If the fixation device 100 encounters an external force, for example, by the distal tip 146 abutting the ossified shell, the flexible tail 140 will redirect the fixation device 100 through the osseous tissue.

Further, a clinician can apply an opposite rotational force to the fixation device 100 to adjust the placement of the fixation device 100 within the osseous tissue or to remove the fixation device 100 completely therefrom.

In a method of using the fixation device 100 in accordance with another embodiment of the present disclosure, an insertion hole is formed in osseous tissue, as described above, and a probe, such as a Lenke style curved probe, is utilized to form a path through the osseous tissue, such as a pedicle of a vertebra. The curved probe may start the insertion hole at the top of an isthmus of the pedicle and bend as the probe approaches cancellous bone to remain within the cortical bone of the osseous tissue.

The fixation device 100, disposed in the initial position of FIGS. 1-3, is inserted into the insertion hole and through the formed path. A tip 66 (FIG. 6B) of a driving instrument 60 may be inserted into the opening 111 defined in the head 110 of the fixation device 100, as described above, to aid in the insertion of the fixation device 100 into the osseous tissue and/or to rotate the fixation device 100 so that the helical threads 132 of the tapered body 130 engage with the osseous tissue (e.g., the pedicle). The flexible tail 140 of the fixation device 100 will follow the pre-defined path (e.g., will not breach the boundary between the cortical bone and the cancellous bone of the osseous tissue). Further, a clinician can apply an opposite rotational force to the fixation device 100 to adjust the placement of the fixation device 100 within the osseous tissue or to remove the fixation device 100 completely therefrom.

Figure 4:
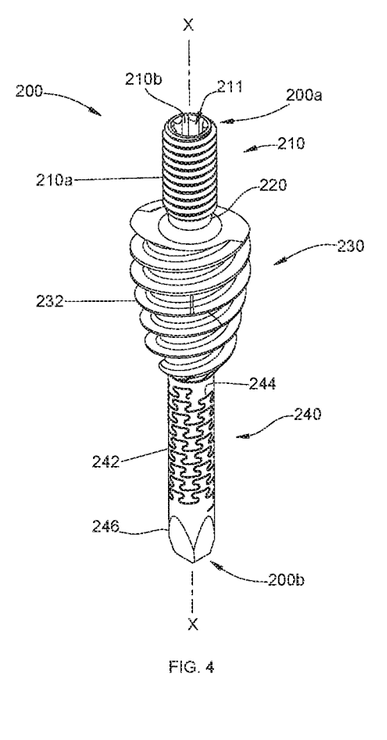
FIG. 4 is a perspective view of a fixation device in accordance with another embodiment of the present disclosure.

With reference now to FIG. 4, a fixation device 200 in accordance with another embodiment of the present disclosure is shown. The fixation device 200 is substantially similar to the fixation device 100 and will be discussed with respect to the differences therebetween. The fixation device 200 extends along a central longitudinal axis "X" and includes a head 210, a neck 220, a tapered body 230, and a flexible tail 240.

The head 210 has a substantially cylindrical shape, and includes a threaded outer surface 210a that is configured for attachment of a complementary inner threaded attachment device (e.g., a modular attachment assembly). The head 210 includes an opening 211 therein that is defined by an inner surface 210b of the head 210. The opening 211 is disposed at a proximal end 200a of the fixation device 200 and is configured and dimensioned to receive the driving instrument 60 (FIG. 6A).

The neck 220 extends between the head 210 and the tapered body 230. The tapered body 230 extends between the neck 220 and the flexible tail 240, and tapers distally towards the flexible tail 240. The tapered body 230 includes exterior helical threads 232 configured to cut and/or thread into osseous tissue.

The flexible tail 240 extends distally from the tapered body 230 to a distal end 200b of the fixation device 200. The flexible tail 240 includes a shaft portion 242 having at least one cut 244 defined therein and a tip portion 246. A central bore (not shown) extends through the fixation device 200 and is concentric with the central longitudinal axis "X".

The fixation device 200 has an initial position in which the flexible tail 240 is aligned with the head 210, the neck 220, and the tapered body 230 along the central longitudinal axis "X", as shown in FIG. 4. The fixation device 200 is movable from the initial position to a variety of deflected positions in which the flexible tail 240 is displaced relative to the central longitudinal axis "X" when and if forces are applied to the flexible tail 140 such as, for example, during insertion of the fixation device 200 into osseous tissue.

The fixation device 200 is positioned within and secured to osseous tissue in a similar manner as discussed above with regard to fixation device 100. Both embodiments are fully inserted into osseous tissue with minimal and/or reduced time and/or effort compared to traditional bone screws. The flexible tail 140, 240 of the fixation device 100, 200 reduces the force required to insert the fixation device 100, 200 into bone and/or allows the fixation device 100, 200 to self-navigate a path through osseous tissue (e.g., a path through cancellous bone which redirects upon contacting cortical bone) or follow a pre-defined path through the osseous tissue (e.g., a curved path through cortical bone) which improves the efficiency of a clinician's insertion of a bone screw into the osseous tissue and therefore successful anchorage to the vertebral body.

The tapered body 130, 230 of the fixation device 100, 200 provides improved toggling strength over a conventional bone screw as the tapered body 130, 230 is engaged with more bone above the pedicle. The tapered body 130, 230 has a greater surface area than a conventional bone screw and thus, may provide improved engagement between the tapered body 130, 230 and the osseous tissue, improved securement of the tapered body 130, 230 in bone, and/or reduced possibility of the fixation device 100, 200 being pulled out of the osseous tissue as compared to traditional bone screws of the same length.

The fixation device 100, 200 may also be used in situations where a hole or an opening exists in a bone with a diameter too large for a traditional bone screw. This may result from a previous bone anchor installation and removal where the opening has a diameter unsuitable for securing a bone screw therein or the opening has an incorrect orientation for proper securement of a bone screw.

Figure 5:
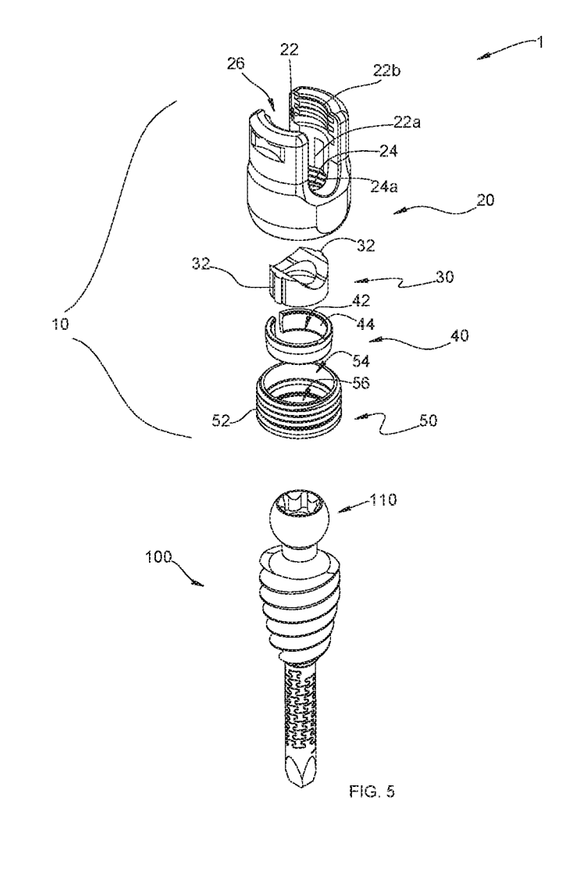
FIG. 5 is a perspective view of a spinal fixation system including the fixation device of FIG. 1 and a modular head assembly, with parts separated, in accordance with an embodiment of the present disclosure.

In embodiments, a surgical device, such as a modular head assembly 10 as shown in FIG. 5, may be coupled to the fixation device 100 such that other surgical devices (e.g., rods, plates, etc.) may be coupled thereto. FIG. 5 illustrates a surgical fixation system 1 including the modular head assembly 10 and the fixation device 100. The modular head assembly 10 includes a housing 20, an anvil 30, a snap ring 40, and an insert 50. The modular head assembly 10 is assembled by aligning a pair of tabs 32 of the anvil 30 with a corresponding pair of slots 22a of a through-hole 22 of the housing 20, and advancing the anvil 30 in a proximal direction within the through-hole 22 such that the pair of tabs 32 engages the pair of slots 22a. Next, the snap ring 40 is placed adjacent a counterbore 24 of the housing 20 and advanced in a proximal direction such that the snap ring 40 is slidably received therein. With the snap ring 40 received within the counterbore 24, the insert 50 is initially placed adjacent the counterbore 24 of the housing 20, and then rotated in a first direction such that a plurality of threads 52 of the insert 50 threadably engages a corresponding plurality of threads 24a of the counterbore 24 of the housing 20. The insert 50 is further rotated until the insert 50 is fully received within the counterbore 24. In this position, the anvil 30 is in a proximal most position and the snap ring 40 is disposed within a first counterbore 54 of the insert 50 such that the snap ring 40 is in a first, uncompressed state.

With the fixation device 100 inserted into bone, as discussed above, the assembled modular head assembly 10 is placed adjacent the head 110 of the fixation device 100. The modular head assembly 10 is then advanced in a distal direction such that the head 110 of the fixation device 100 is received within a bore 56 of the insert 50, and thereafter, within a lumen 42 of the snap ring 40. As the head 110 of the fixation device 100 advances within the lumen 42 of the snap ring 40, the head 110 causes the snap ring 40 to expand (e.g., the diameter enlarges) to accept the head 110 therein. A concave inner surface 44 of the lumen 42 conforms to the spherical profile of the head 110 such that the diameter of the snap ring 40 reduces from an expanded state during insertion of the head 110 therein to a compressed state where the inner diameter of the lumen 42 conforms to the diameter of the head 110 and provides a compressive force thereon. Thereafter, the axial orientation of the fixation device 100 relative to the modular head assembly 10 may be adjusted and locked, for example, when a suitable spinal rod (not shown) is secured within a U-shaped slot 26 of the housing 20 using a suitable set screw (not shown) threadingly engaged with a plurality of threads 22b of the through-hole 22 of the housing 20.

Figure 6B:
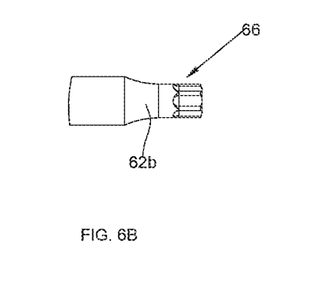
FIG. 6B is an enlarged view of the area of detail in FIG. 6A.

With reference to FIGS. 6A and 6B, a driving instrument or driver suitable for use with either the fixation device 100 or the fixation device 200 is provided and generally identified by reference numeral 60. The driving instrument 60 includes an elongate shaft 62 having a proximal portion 62a and an opposed distal portion 62b. The proximal portion 62a of the elongate shaft 62 defines a handle 64 that is configured to enable selective rotation of the driving instrument 60 (e.g., by gripping the handle 64 and applying rotational force thereto) by a clinician. The distal portion 62b of the driving instrument 60 tapers to a driving, but reduced diameter engagement region or tip 66. The engagement region 66 includes protrusions and recesses that are complementary to the opening 111, 211 of the head 110, 210 of the fixation device 100, 200. Once the engagement region 66 is inserted into the opening 111, 211, rotation of the driving instrument 60 results in rotation of the fixation device 100, 200. Thus, the driving instrument 60 is capable of rotating the fixation device 100, 200 for insertion or removal of the fixation device 100, 200 into bone. It is envisioned that driving instrument 60 may also be used with a set screw (not shown) for inserting and/or removing the set screw from the housing 20 of the modular head assembly 10.

Persons skilled in the art will understand that the structures and methods specifically described herein and shown in the accompanying figures are non-limiting exemplary embodiments, and that the description, disclosure, and figures should be construed merely as exemplary of particular embodiments. It is to be understood, therefore, that the present disclosure is not limited to the precise embodiments described, and that various other changes and modifications may be effected by one skilled in the art without departing from the scope or spirit of the disclosure. Additionally, the elements and features shown and described in connection with certain embodiments may be combined with the elements and features of certain other embodiments without departing from the scope of the present disclosure, and that such modifications and variation are also included within the scope of the present disclosure. Accordingly, the subject matter of the present disclosure is not limited by what has been particularly shown and described. Thus, other embodiments are within the scope of the following claims.

What is claimed is:

1. A fixation device comprising:
   a head;
   a tapered body coupled to the head and extending distally from the head along a central longitudinal axis; and
   an unthreaded flexible tail extending distally from the tapered body, the flexible tail defining a central bore therethrough, the flexible tail movable from an initial configuration aligned with the central longitudinal axis to a deflected configuration that extends away from the central longitudinal axis when a force is applied to the flexible tail.

2. The fixation device according to claim 1, wherein the head portion defines an opening therein.

3. The fixation device according to claim 1, further comprising a neck interconnecting the head and the tapered body.

4. The fixation device according to claim 1, wherein the tapered body includes helical threads disposed on an outer surface thereof, tapering distally towards the flexible tail.

5. The fixation device according to claim 1, wherein the tapered body has a length extending at least a quarter of an overall length of the fixation device.

6. The fixation device according to claim 1, wherein the tapered body has a length extending at least a half of an overall length of the fixation device.

7. The fixation device according to claim 1, wherein the flexible tail includes a shaft portion having a cut formed therein following a helical path around the shaft portion.

8. The fixation device according to claim 7, wherein the cut extends from a proximal end to a distal end of the shaft portion of the flexible tail.

9. The fixation device according to claim 7, wherein the cut defines alternating trapezoidal shapes along the shaft portion.

10. The fixation device according to claim 7, wherein the flexible tail includes a tip portion extending distally from the shaft portion.

11. The fixation device according to claim 10, wherein the tip portion tapers distally to a distal end of the fixation device.

12. The fixation device according to claim 11, wherein the tip portion includes a plurality of facets defining edges therebetween.

13. The fixation device according to claim 1, wherein the flexible tail has a length extending at least a quarter of an overall length of the fixation device.

14. The fixation device according to claim 1, wherein the flexible tail has a length extending at least a half of an overall length of the fixation device.

15. The fixation device according to claim 2, wherein the central bore is disposed distal to and in fluid communication with the opening of the head and extends to a distal end of the fixation device.

16. The fixation device according to claim 1, wherein the central bore includes a proximal portion having a first diameter and a distal portion having a second diameter smaller than the first diameter.

17. The fixation device according to claim 16, wherein the proximal portion of the central bore is disposed within a shaft portion of the flexible tail, and the distal portion of the central bore is disposed within a distal tip of the flexible tail.

18. The fixation device according to claim 1, wherein the head portion has a cylindrical shape including a threaded outer surface.

* * * * *